United States Patent [19]

Sethi

[11] Patent Number: 5,406,193

[45] Date of Patent: Apr. 11, 1995

[54] HOT GAS IN-SITU MONITORING PROBE

[75] Inventor: Vijay K. Sethi, Laramie, Wyo.

[73] Assignee: Western Research Institute, Laramie, Wyo.

[21] Appl. No.: 81,775

[22] Filed: Jun. 23, 1993

[51] Int. Cl.6 ............................................. G01N 27/02
[52] U.S. Cl. .................................. 324/71.1; 324/663; 324/693; 356/36
[58] Field of Search ............... 324/663, 686, 693, 722, 324/71.1, 71.4; 356/36

[56] References Cited

U.S. PATENT DOCUMENTS

| | | | |
|---|---|---|---|
| 3,957,374 | 5/1976 | Kriese et al. | 356/36 X |
| 4,491,786 | 1/1985 | Godin | 324/71.1 |
| 4,677,426 | 6/1987 | Dattilo | 324/71.4 X |
| 5,143,696 | 9/1992 | Haas et al. | 324/663 X |
| 5,282,381 | 2/1994 | Krone-Schmidt | 324/663 X |

OTHER PUBLICATIONS

S. Lee et al, "Measurement of Alkali Vapor Concentration in PFBC Flue Gas," Proc. 1989 International Conf. on Fluidized Bed Combustion, ASME, 977–985, May 1989.

H. Spacil et al, "Volatilization/Condensation of Alkali Salts in a Pressured Fluidized Bed Coal Combustor/Gas Turbine Combined Cycle," J. Electrochem. Soc., 129, 2119–2126, Sep. 1982.

W. Hass et al, "Fiber Optic Alkali Meter Sampling," Proc. 7th Annual Coal-Fueled Heat Engines and Gas Stream Cleanup Systems Review Meeting, DOE/METC-90/6110, 391–402, Mar. 1990.

Primary Examiner—Kenneth A. Wieder
Assistant Examiner—Glenn W. Brown
Attorney, Agent, or Firm—John O. Mingle

[57] ABSTRACT

A probe for real-time in-situ monitoring for hot gas contaminants, such as alkali, uses the detection principles of condensation/vaporization temperatures or corrosion rates with electrical/optical measurements.

12 Claims, 2 Drawing Sheets

HOT GAS IN-SITU MONITORING PROBE

BACKGROUND OF INVENTION

1. Field of Invention

The present invention relates to real-time in-situ monitoring of contaminants, such as alkali compounds, from a hot gas stream.

2. Background

The increasing use of dirty fuels for firing gas turbines for many applications requires the monitoring of gas contaminants that degrade the turbine performance by deposition, erosion and corrosion. Various contaminants can cause degradation, such as alkali compounds.

Alkali is the most common contaminant which causes severe degradation of turbine gas path components, and has a declared tolerance level of about 0.024 ppm for gases entering industrial turbines. This consideration arises because alkali salts, such as sulfates, cause sever corrosion of turbine parts when condensed on the gas path components. As the reserves of clean fuels are decreasing, turbine systems are operating with increasingly dirtier fuels which enhances the likelihood of such corrosion.

Coal-fired systems are formulated where pressurized coal combustion gases pass through a gas turbine. Coal combustion gases are reported to have alkali concentrations of from 0.05 ppm to several ppm; see S. Lee, et al., "Measurement of Alkali Vapor Concentration in PFBC Flue Gas," Proceedings of 1989 International Conference on Fluidized Bed Combustion, ASME, pp 977–985, May 1989; hereinafter Lee (1989). Various physical and chemical systems can potentially remove such excess contaminants from pre-turbine hot gases; however, the key is still the appropriate detection of contaminant amounts.

Another dirty hot gas environment is that from the combustion of municipal solid wastes where heavy elements, usually in the form of salts, are potentially a concern. Such salts cause severe corrosion of waterwall tubes, superheater tubes and other components.

Current alkali monitors are based upon several procedures. Extractive condensation employs a filter to remove particulate matter followed by a cold trap and water bubblers to condense alkali compounds; see H. Spacil, et al., "Volatization/Condensation of Alkali Salts in a Pressured Fluidized Bed Coal Combustor/Gas Turbine Combined Cycle," J. Electrochem. Soc., 129, pp 2119–2126, September 1982.

Sorber beds employ activated bauxite or diatomaceous earth to remove alkali from a slip stream followed by water leaching and conventional wet analysis of the sorber bed materials; see Lee (1989).

Vapor monitors employ flame emission spectroscopy applied to a slip stream; see W. Hass, et al., "Fiber Optic Alkali Meter Sampling," Proceeding of the Seventh Annual Coal-Fueled Heat Engines and Gas Stream Cleanup Systems Review Meeting, Editors H. Webb, et al., DOE/METC-90/6110, pp 391–402, Mar. 1990.

Much variability is shown by comparisons between these above methods, and potentially sampling line losses may represent a plausible source for these discrepancies. None of these methods employ real-time in-situ measurement which negates sampling line problems.

SUMMARY OF INVENTION

The objectives of the present invention include overcoming the above-apparent deficiencies in the prior art by providing a probe that in-situ determines quantitatively contaminants for a hot gas stream by employing dew point measurements.

DETAILED DESCRIPTION OF INVENTION

Figure 1:
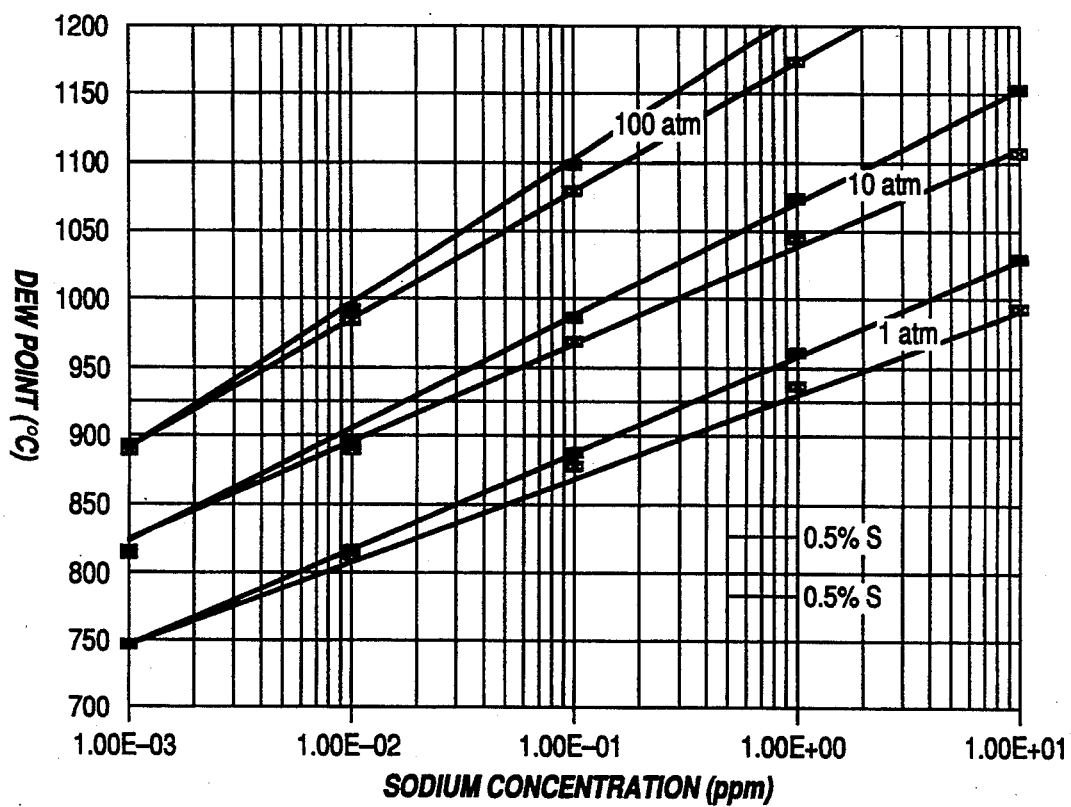
FIG. 1 shows a sodium sulfate dew point graph.

Hot gas contaminants are potentially a wide variety of elements, compounds or other materials that are degrading to the materials employed in turbines, blowers, compressors, and other power generating equipment exposed to combustion gases. Alkali metal compounds, commonly called alkali, are frequent contaminants of concern in gas turbine systems, and generally refer to various constituents of potassium and sodium. Alkali contaminants usually appear in the form of compounds comprising sulfates, oxides, hydroxides, chlorides, silicates and aluminosilicates. Some other contaminants of concern in combustion systems other than gas turbines are heavy metals, such as zinc, antimony, arsenic, cadmium, lead, and their respective salts. Sulfur in the form of sulfates and chlorine in the form of chlorides are also considered contaminants.

Fuel bound contaminants enter the gas phase as volatile compounds. In gas turbine systems the stable alkali compounds are usually sodium and potassium sulfates; however, alkali also exist in the gas phase as chlorides. The amount of alkali present in the gas phase is determined by the alkali and sulfur content of the fuel. Heavy metal contaminants exist in the gas phase as chlorides and sulfates; however, they are typically not encountered in gas turbine systems but frequently occur in municipal waste-fired steam plants. This invention determines the concentration of all of these vapor phase contaminants.

To effectively measure the consequence of contaminants in a hot gas stream, some chemical or physical effect for an in-situ probe is changed by such exposure; thus, the probe utilizes the variability of measurements over a plurality of detection elements as the contaminants cause the physical nature of said elements to change. A feasible approach is the affect of liquid condensation, or other phase change, of such contaminants upon said probe as it changes electrical resistivity either by shorting out electrical contacts or by corroding such probe and changing its response. An alternate approach is to measure electrical capacitance between elements and this changes with contaminant collection. For such condensation to occur a surface temperature below the dew point of a given contaminant in the hot gas stream is necessary; thus, a heat transfer mechanism sets up a temperature gradient upon the probe that includes the needed dew point temperature.

A heat transfer system operates with a coolant fluid, often air, to produce the needed temperature gradient across the probe surface. The probe is exposed to the hot gas stream so employing a controlled coolant fluid separated from the probe monitor elements by a heat-passing barrier produces the needed temperature gradient. The type, amount and temperature of coolant is adjusted to create the needed contaminant dew point temperature within the boundaries of the measuring plurality of attached elements to the probe base. Alternatively other heat transfer systems might involve heating for evaporation or melting and other cooling mechanisms for condensation besides fluids, such as solid state cooling devices.

Generalizing this concept makes any change of phase of contaminant because of an imposed temperature gradient a mechanism to change physical measurements associated with the plurality of attached elements; wherein said change of phase is selected from the group comprising condensing, vaporizing, melting, solidifying, subliming, and combinations thereof.

EXAMPLE 1

For sodium sulfate vapor as the contaminant, FIG. 1 shows a typical plot of fuel sodium concentration versus dew point temperature for various total pressures for two fuel sulfur concentrations. For instance, the 0.024 ppm or 24 ppb concentration at ten atmospheres total pressure represents a dew point in the range of about 920° to 930° C. depending upon the fuel sulfur concentration. In order to determine reasonable parts per billion concentrations, it is desirable to utilize a detection system that produces an accuracy within about 5 ppb. Therefore the detection of liquid alkali, such as liquid sodium sulfate, at a given measured probe temperature represents the dew point temperature from which the contaminant concentration in the vapor phase is determined to this desired accuracy. If the contaminant is an another alkali salt, a dew point chart or its equivalent is constructed for the specific compound of interest instead of the sodium sulfate of FIG. 1. Vapor pressure information for a given contaminant either is commonly available or is routinely measured.

EXAMPLE 2

Figure 2A:
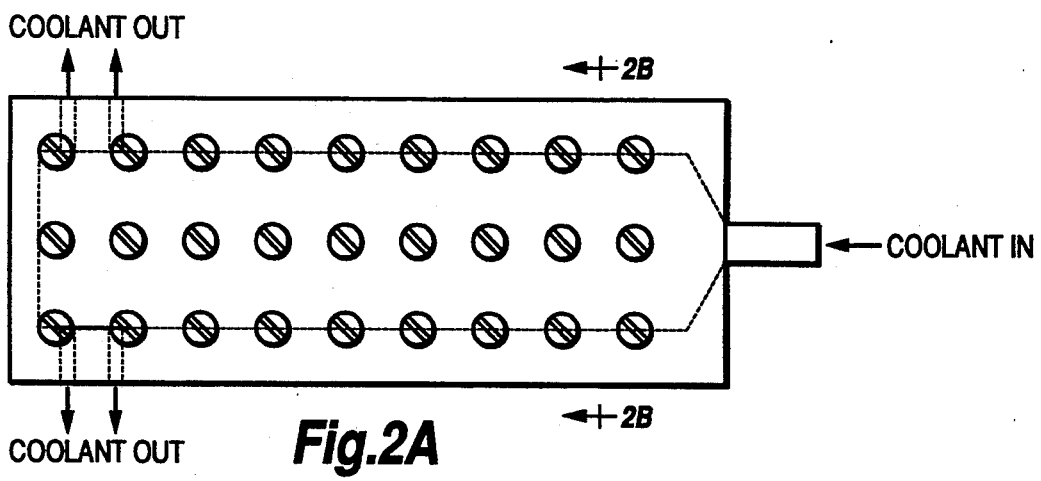
FIG. 2 shows a probe layout utilizing small disks for detention elements with a base capable of heat transfer.
Figure 2B:
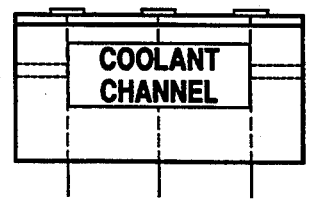
Figure 3:
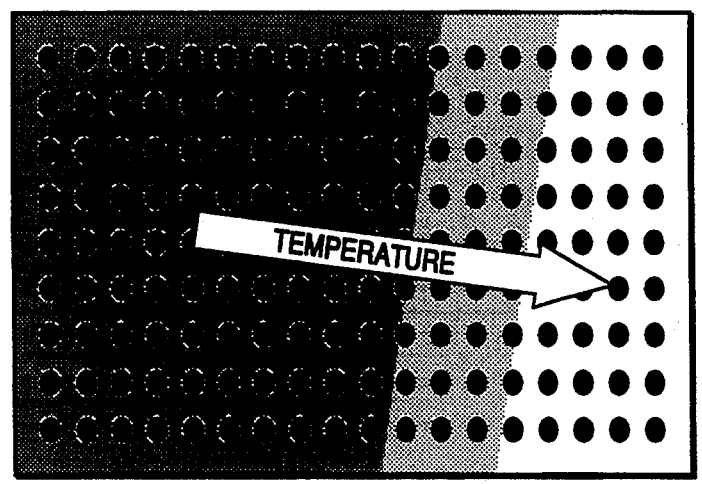
FIG. 3 shows a probe, utilizing small disk for detection elements, resistivity map.

A monitoring probe to detect alkali, such as sodium sulfate vapor, in hot gas is shown in FIG. 2 comprising a plurality of small metal or other stable or fixed electrical characteristic elements attached on an electrically insulating base. The attachment is firm enough so that the elements maintain good thermal contact with the base in order that good heat transfer occurs. Besides serving as an electrical insulator, said base is relatively inert to the environment of the hot turbine inlet gas which is potentially more than 1200° C. and can contain corrosive contaminants. In FIG. 2 each element is a metal disk, usually smaller than about seven millimeters in diameter although size is not critical, positioned in a compact array grid, preferably square, having a minimum of one millimeter distance between elements with an electrical connection on the reverse side through the base that further serves as a high temperature measuring thermocouple. Platinum platinum-rhodium is often employed at these temperatures as the thermocouple material. Normally the plurality of attached elements have a high resistivity between them. As shown in FIG. 3, a temperature gradient is maintained by heat transfer, in this case a coolant flow, through the reverse side of the base, and zone A is above the vapor phase dew point of the alkali compound, in this case sodium sulfate. Zone B is below this dew point but above the freezing temperature and contains liquid sodium sulfate, electrically shorting the elements. Zone C is below the sodium sulfate freezing temperature and contains solid sodium sulfate deposited upon the element grid. Appropriate dynamic temperature and resistivity measurements using conventional electronics determines these regions. From the temperature measurements the liquid dew point and thus the concentration of specific alkali in the hot gas, as shown in Example 1, is determined.

EXAMPLE 3

A monitoring probe was constructed on a ceramic base of alumina about $1 \times \frac{1}{2} \times \frac{1}{8}$ inches using painted strips of gold to produce small interspaced fingers, approximately 0.063 inches, about 1.6 mm, in width, positioned nearly the same distance apart in a parallel grid forming an effective 7×2 array. Ceramic bonding material attached gold wires to the fingers. In order to maintain a temperature gradient, a heat transfer system, in this case air cooling, was contained in a stainless steel block with passages and attached to the ceramic base. The thermocouple wire connections were type K. The electrical monitoring was performed with a conventional electronic equipment representing a resistance bridge measurement.

A probe was made using a change of phase, in this case melting, by painting the element array grid with a band of dissolved salt leaving a solid residue. Both sodium chloride and a 4:1 mixture of sodium sulfate and potassium sulfate were employed. Heating was allowed up to a gas temperature of 1750° F., but above the melting temperature of the salt mixture left a liquid band covering the plurality of attached elements because of the air coolant flow. Electrical resistance measurements between adjacent elements were more than 5000 ohm unless the liquid salt was present which reduced such measurements to a range of about 50 to 500 ohm. This resistance profile was movable to different elements by changing the coolant rate.

Table 1 resistance measurements results were for sodium chloride and the probe verified that NaCl melted at about the handbook value of 1474° F. Similar Table 2 results were for the 4:1 sodium sulfate and potassium sulfate mixture, and from the results its melting temperature was estimated as about 1717° F. Here the high resistance reading for the hottest element suggested that some evaporation had occurred. In both instances accuracy was potentially improvable by adjusting the cooling system to spread out the liquid salt band over several elements. Further additional numerical analysis of the data could produce an improved estimate of the desired phase change, or in this case melting point, temperature.

The integrity of the probe was limited as the liquid sulfate salts corroded the gold paint; however, use of platinum appeared feasible to extend the life such a probe.

EXAMPLE 4

A probe similar to that of Example 3 is used except in the form of a disk grid. The probe is exposed to various known concentrations of sodium chloride or other alkali compound vapor at up to 950° C. at nominal pressure and cooled with air through a passage associate with the ceramic base. Measurement of resistivity between elements create a resistivity map caused by band alkali condensation similar to that of FIG. 3.

Concurrently temperatures are measured by thermocouples so that by comparison with the resistivity map, the liquid dew point region is confirmed. The dew point and appropriate concentration is verified to within an accuracy of about ±5 ppb.

TABLE 1

Test Data for Sodium Chloride

| Element Temperature (°F.) | Adj. Element Resistance (ohm) |
|---|---|
| 1503 | 86 |
| 1501 | 86 |
| 1498 | 87 |
| 1477 | 95 ← |
| 1465 | 550 |
| 1450 | 1125 |
| 1430 | 2250 |
| 1405 | 21000 |

TABLE 2

Test Data for 4:1 Sodium Sulfate and Potasium Sulfate Mixture

| Element Temperature (°F.) | Adj. Element Resistance (ohm) |
|---|---|
| 1735 | 9000 |
| 1717 | 50 ← |
| 1706 | 500 |
| 1685 | 3500 |
| 1674 | 6000 |
| 1662 | 13500 |
| 1650 | 16000 |

EXAMPLE 5

A probe similar to that in Example 3 is used except with platinum disks as the probe elements. The thermocouple wire is platinum with 10%-rhodium giving each element a platinum—platinum-rhodium thermocouple connection. The probe is exposed to sodium chloride or other alkali vapor at 950° C. at nominal pressure and cooled with air through a passage associated with the ceramic base. The temperatures are measured with thermocouples and create a band resistivity map caused by condensation. The dew point and appropriate concentration are determined.

EXAMPLE 6

A probe similar to that in Example 3 is used and exposed to a combustion environment from municipal solid waste where heavy elements are potentially a concern. Vapor phase $PbCl_3$ and other contaminant salts, which cause severe corrosion of water-wall tubes, superheater tubes and other components, are detected in the manner as provided for in Examples 3 to 5.

EXAMPLE 7

A monitoring probe to detect a poor conductor contaminant when condensed, such as sulfur or a metal that quickly oxides when condensed, uses electrical capacitance measurement changes. Such a probe comprises a plurality of small metal elements attached on an electrically insulating base similar to Example 2. Each element is a small metal finger usually about a few millimeters across although size is not critical, positioned in a compact parallel grid of interspaced fingers. The meaning of interspaced fingers is an arrangement of fingers alternately originating from each side of the probe. The fingers are a minimum of one millimeter distance between elements with an electrical connection on the reverse side through the base that further serves as a high temperature measuring thermocouple. Platinum—platinum-rhodium is often employed at these temperatures as the thermocouple material. Normally the plurality of attached elements have an easily measured capacitance between them. Appropriate dynamic temperature and capacitance measurements using conventional electronics determines where band condensation has occurred which changes the measurement of capacity between such elements. From the temperature measurements the liquid dew point and thus the concentration of contaminant in the hot gas is determined.

EXAMPLE 8

An alternate probe approach uses contaminants which corrode metal alloy elements used for the physical measurements over a plurality of such attached elements superimposed on an appropriate inert base and is composed of selected metal alloys, preferably a form of stainless steel, or similar high temperature alloy, that is chemically attacked by said contaminant at the conditions for which the probe is exposed. The tradeoff is between material that suffer rapid corrosion which enhances the accuracy and slower corrosion which makes for long probe life. Alkali liquid salts at these high dew point temperatures will rapidly corrode such metal alloy elements and change their resistance measurements; thus, the rate of resistance change will correlate with the corrosion rate and identify the presence of liquid alkali salts.

Figure 4A:
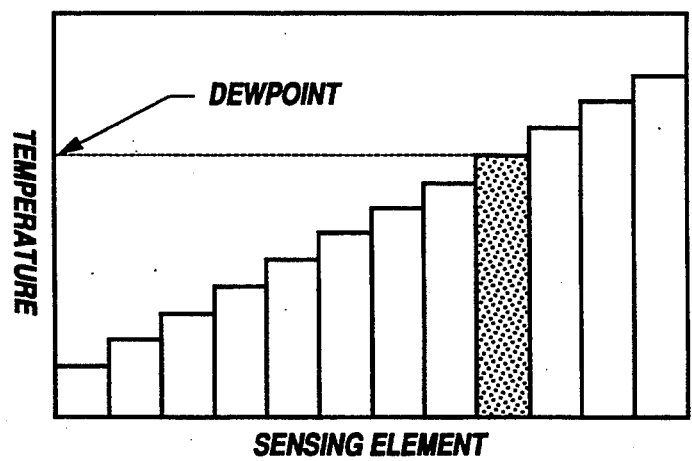
FIG. 4A shows an element temperature diagram.
Figure 4B:
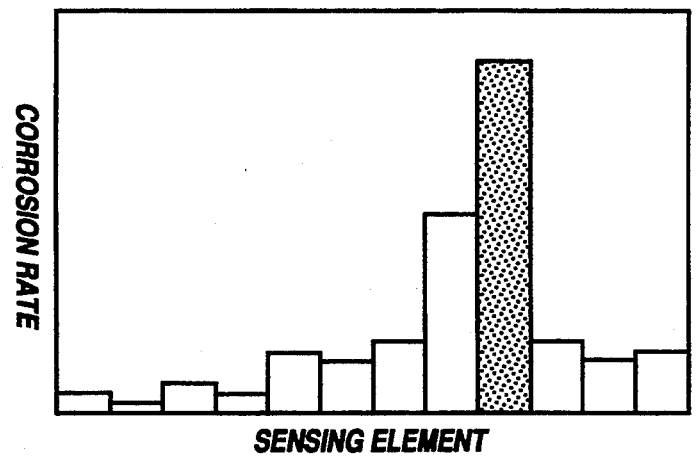
FIG. 4B shows an element corrosion rate diagram.

The element grid is composed of a series of fine wires, smaller than about 16 gauge with about 1 mm spacing, attached parallel across the width of the probe and ideally running perpendicular to the temperature gradient. The thickness of the wires is a tradeoff as thicker wires are more rugged and last longer but for a given rate of corrosion, show a smaller change in resistance, and a decrease in accuracy. The wires cooled to below the dew point temperature has liquid alkali salts condensed on them causing corrosion and an appropriate change in their resistance. Concurrent thermocouple measurements determine this dew point corrosion region temperature as is represented in FIG. 4. FIG. 4A shows a bar graph of temperatures for such elements. FIG. 4B gives the Corresponding determined corrosion rates and the shaded element represents the liquid band region of high corrosion. Concentration calculations are then made for the appropriate alkali salt. Alternatively the measurements consist of electrical capacitance changes such as Example 7.

EXAMPLE 9

An approach similar to Example 8 is used to measure vapor phase concentration of contaminant compounds, such as $PbCl_3$, as was explained in Example 6, in combustion gases from a municipal solid waste incinerator or coal combustor where heavy elements are a concern. Dew points of said compounds are measured by identifying the elements which corrode at high rates from measurements of changes in resistance of said elements which are held at near the melting temperature of said compounds.

EXAMPLE 10

Similar to Example 8 a further alternate approach for a monitoring probe is constructed of optical fiber elements attached on an optically inert base using conventional fine optical fibers, preferably smaller than about 20 gauge like is commonly utilized in fiber optic communication equipment. The thickness of the elements is a tradeoff as thicker fibers are more rugged and last longer but will suffer a lower rate of corrosion, a lower rate of change of optical characteristic, and a decrease in accuracy. The condensed liquid alkali salt now corrodes these optical elements such that measurements of said optical characteristic, such as reflectance or transmission, are changed. Appropriate thermocouples measure this dew point corrosion region temperature. Concentration calculations are then made.

EXAMPLE 11

An alternate heat transfer system is employed wherein maintaining or having a temperature gradient is done by utilizing thermocouples in their inverse mode as a thermoelectric cooling device. That is, passing appropriately direct current through said thermocouples so as to produce a cooling effect. Generally the more current employed, the higher the cooling rate. Some thermocouples are permanently used in this manner and others are potentially switched to the reverse temperature measuring mode upon demand to determine temperatures and their subsequent gradient.

The foregoing description of the specific embodiments will so fully reveal the general nature of the invention that others can, by applying current knowledge, readily modify and/or adapt for various applications such specific embodiments without departing from the generic concept, and therefore such adaptations or modifications are intended to be comprehended within the meaning and range of equivalents of the disclosed embodiments. It is to be understood that the phraseology or terminology herein is for the purpose of description and not of limitation.

I claim:

1. An in-situ monitoring probe for detecting hot gas contaminants comprising:
    an inert base projecting into said gas and having a temperature gradient produced by heating, cooling, or combinations thereof;
    a plurality of detection elements superimposed upon said base and creating good thermal contact; and
    measurements on said elements made by said means for detecting a change of phase of said contaminants by measuring the variability of said elements wherein said measuring is selected from the group consisting essentially of electrical resistivity, electrical capacitance, optical reflectance, optical conductance, and combinations thereof.

2. The probe according to claim 1 wherein the temperature where said change of phase occurs further indicates the concentration of said contaminants of employing vapor pressure data.

3. The probe according to claim 1 wherein said contaminants further comprise being selected from the group consisting essentially of alkali, heavy elements, sulfur, chlorine, and combinations thereof.

4. The probe according to claim 1 wherein said plurality of detection elements further comprises a fine detection grid, with the spacing between said elements greater than about one millimeter, being selected from the group consisting essentially of fine fibers, smaller than about 20 gauge, positioned in a narrow parallel grid; small disks, smaller than about seven millimeters in diameter, positioned in a compact array grid; interspaced fingers a few millimeters in width positioned in a parallel grid; and combinations thereof.

5. The probe according to claim 1 wherein said change of phase is selected from the group consisting essentially condensing, vaporizing, melting, solidifying, subliming, and combinations thereof.

6. A hot gas probe for monitoring vapor phase contaminants comprising:
    an electrically inert base projecting into said gas and having a temperature gradient produced by;
    a plurality of detection elements, having stable electrical characteristics, superimposed upon said base and creating good thermal contact; and means for detecting said contaminants by measuring the variability of said elements wherein said measuring is selected from the group consisting essentially of electrical resistivity, electrical capacitance, and combinations thereof, and wherein said vaporization, corrosion, and combinations thereof.

7. The probe according to claim 6 wherein the temperature where said condensation or vaporization occurs further indicates the concentration of said contaminants by employing vapor pressure data.

8. The probe according to claim 6 wherein said contaminants further comprise being selected from the group consisting essentially of alkali, heavy elements, sulfur, chlorine, and combinations thereof.

9. The probe according to claim 6 wherein said plurality of detection elements further comprises a fine detection grid, with the spacing between said elements no closer than about one millimeter, being selected from the group consisting essentially of fine fibers, smaller than about 20 gauge, positioned in a narrow parallel grid; small disks, smaller than about seven millimeters in diameter, positioned in a compact array grid; interspaced fingers a few millimeters in width positioned in a parallel grid; and combinations thereof.

10. A hot gas probe for monitoring vapor phase contaminants comprising:
    an optically inert base projecting into said gas and having a temperature gradient produced by heating, cooling, or combinations thereof;
    a plurality of optical fiber elements superimposed upon said base creating good thermal contact, and wherein the spacing between said elements is greater than about one millimeter; and
    means for detecting said contaminants by measuring the variability or said element wherein said measuring is selected from the group consisting essentially of optical transmission, optical reflectance, and combinations thereof, and wherein said variability consists of condensation, vaporization, corrosion, and combinations thereof.

11. The probe according to claim 10 wherein the temperature where said condensation or vaporization occurs further indicates the concentration of said contaminants by employing vapor pressure data.

12. The probe according to claim 10 wherein said contaminants further comprise being selected from the group consisting essentially of alkali, heavy elements, sulfur, chlorine, and combinations thereof.

* * * * *